(12) United States Patent
Clavaguera et al.

(10) Patent No.: US 9,849,414 B2
(45) Date of Patent: Dec. 26, 2017

(54) FILTRATION ASSEMBLY COMPRISING A FILTER AND A FILTER SUPPORT AND ASSOCIATED METHOD FOR THE COLLECTION AND ANALYSIS OF NANOPARTICLES

(71) Applicants: COMMISSARIAT A L'ENERGIE ATOMIQUE ET AUX ENERGIES ALTERNATIVES, Paris (FR); NANOINSPECT, Peronnas (FR)

(72) Inventors: Simon Clavaguera, Alenya (FR); Eric Decolin, Montbonnot Saint Martin (FR); Arnaud Guiot, Saint Egreve (FR); Guillaume Hebert, La Tronche (FR); Sebastien Jacquinot, Chatuzange-le-Goubet (FR); Sylvie Motellier, Saint-Laurent-du-Pont (FR)

(73) Assignees: COMMISSARIAT À L'ENERGIE ATOMIQUE ET AUX ENERGIES ALTERNATIVES, Paris (FR); NANOINSPECT, Peronnas (FR)

( * ) Notice: Subject to any disclaimer, the term of this patent is extended or adjusted under 35 U.S.C. 154(b) by 0 days.

(21) Appl. No.: 14/410,499

(22) PCT Filed: Jun. 12, 2013

(86) PCT No.: PCT/IB2013/054807
§ 371 (c)(1),
(2) Date: Dec. 22, 2014

(87) PCT Pub. No.: WO2014/001936
PCT Pub. Date: Jan. 3, 2014

(65) Prior Publication Data
US 2015/0251119 A1    Sep. 10, 2015

(30) Foreign Application Priority Data

Jun. 20, 2012 (FR) ..................... 12 55785

(51) Int. Cl.
*B01D 69/10* (2006.01)
*B01D 46/00* (2006.01)
(Continued)

(52) U.S. Cl.
CPC ....... *B01D 46/0005* (2013.01); *B01D 46/009* (2013.01); *B01D 46/247* (2013.01);
(Continued)

(58) Field of Classification Search
CPC ...... B01D 46/009; B01D 71/50; B01D 71/56; B01D 2201/04; B01D 2201/0415;
(Continued)

(56) References Cited

U.S. PATENT DOCUMENTS 3,932,153 A * 1/1976 Byrns ............... A61M 16/1055
128/205.29
4,148,732 A * 4/1979 Burrow ............. A61M 16/1055
210/232
(Continued)

FOREIGN PATENT DOCUMENTS

DE   10 2008 006 320 A1   7/2009
FR       2 662 635 A1     12/1991
(Continued)

OTHER PUBLICATIONS

International Search Report issued in International Patent Application No. PCT/IB2013/054807 dated Nov. 29, 2013.
(Continued)

*Primary Examiner* — Joseph C Rodriguez
(74) *Attorney, Agent, or Firm* — Oliff PLC (57) ABSTRACT

A filtration assembly for filtering nanoparticles includes a filter having pores that can retain nanoparticles likely to be found in an air flow passing through the filter and a filter support including two parts. A lower base-forming part of the filter support includes a peripheral bearing surface on
(Continued)

which the filter can rest. An upper ring-shaped part of the filter support is designed to be mounted around the bearing surface of the base. By mounting the ring around the bearing surface of the base it is possible to tension the filter radially to the direction of mounting. The mounting clearance between the ring and the bearing surface of the base is dimensioned such as to maintain the filter resting on the bearing surface under mechanical stress by means of pinching, in a direction radial to the mounting direction.

16 Claims, 5 Drawing Sheets

(51) Int. Cl.
    *B01D 63/08*     (2006.01)
    *B01D 46/24*     (2006.01)
    *G01N 23/223*     (2006.01)
    *G01N 15/00*     (2006.01)

(52) U.S. Cl.
    CPC ........... *B01D 63/087* (2013.01); *B01D 69/10* (2013.01); *G01N 23/223* (2013.01); *G01N 2015/0038* (2013.01); *Y10T 29/53796* (2015.01); *Y10T 29/53848* (2015.01)

(58) Field of Classification Search
    CPC .......... B01D 2313/02; B01D 2313/025; B01D 2201/4084; B01D 63/087; B01D 69/10; B07B 1/06; B07B 2201/02
    USPC ................................................. 977/707, 845
    See application file for complete search history.

(56) References Cited

U.S. PATENT DOCUMENTS

| | | | |
|---|---|---|---|
| 4,362,047 A | | 12/1982 | Vonreis et al. |
| 4,514,300 A | * | 4/1985 | Szczesny ................ B07B 1/06 210/342 |
| 4,544,386 A | * | 10/1985 | Trayford, III .......... B01D 46/10 55/503 |
| 4,755,287 A | * | 7/1988 | Jones ........................ B07B 1/06 209/235 |
| 4,961,916 A | | 10/1990 | Lesage et al. |
| 5,171,445 A | * | 12/1992 | Zepf ..................... B01D 53/228 210/500.27 |
| 5,688,460 A | * | 11/1997 | Ruschke ............. A61M 1/3627 264/263 |
| 6,033,455 A | * | 3/2000 | Kurashima ......... A61M 16/105 210/445 |
| 6,120,875 A | | 9/2000 | Haumont et al. |
| 6,523,367 B1 | | 2/2003 | Ikeda et al. |
| 6,672,135 B2 | * | 1/2004 | Adiletta ............... B01D 46/543 210/321.84 |
| 6,779,411 B1 | | 8/2004 | Spurgeon |
| 6,779,669 B2 | * | 8/2004 | Schann ................. B01D 29/012 210/446 |
| 6,846,412 B2 | * | 1/2005 | Hogan ................... B01D 29/01 210/227 |
| 7,279,134 B2 | * | 10/2007 | Chan ..................... B01D 61/022 216/2 |
| 7,582,146 B2 | * | 9/2009 | Lai ..................... B01D 46/0041 55/503 |
| 8,906,234 B2 | * | 12/2014 | Yamamoto ............. B01D 39/06 210/321.6 |
| 9,156,006 B2 | * | 10/2015 | Yip ...................... B01D 61/002 |
| 2003/0020024 A1 | | 1/2003 | Ferain et al. |
| 2006/0278580 A1 | * | 12/2006 | Striemer ................ B01D 61/18 210/650 |
| 2008/0072764 A1 | | 3/2008 | Lai et al. |
| 2008/0307971 A1 | * | 12/2008 | Horie .................. B01D 39/1623 95/287 |
| 2010/0322825 A1 | * | 12/2010 | Yamakawa ........ B01L 3/502761 422/82.05 |
| 2011/0042301 A1 | * | 2/2011 | Zhang .................. B01D 67/006 210/500.21 |
| 2011/0152107 A1 | * | 6/2011 | McGrath ................ B01D 57/02 506/7 |
| 2012/0080361 A1 | * | 4/2012 | Walavalkar ........ B01D 67/0062 209/235 |
| 2012/0097603 A1 | | 4/2012 | Ichinose et al. |
| 2012/0097610 A1 | * | 4/2012 | Zheng .................... B01D 61/18 210/650 |
| 2012/0151889 A1 | * | 6/2012 | Horey .................... B01D 46/10 55/467 |
| 2012/0205306 A1 | * | 8/2012 | Reich .................... A61M 1/3472 210/519 |
| 2012/0318729 A1 | * | 12/2012 | Yip ...................... B01D 61/002 210/490 |
| 2013/0256230 A1 | * | 10/2013 | Dullaert ............... G01N 33/491 210/650 |
| 2014/0021133 A1 | * | 1/2014 | Siwy .................. B01D 67/0062 210/650 |

FOREIGN PATENT DOCUMENTS

| | | |
|---|---|---|
| FR | 2 803 238 A1 | 7/2001 |
| WO | WO 98/08072 A1 | 2/1998 |
| WO | WO 01/51177 A1 | 7/2001 |
| WO | WO 2006/119301 A2 | 11/2006 |

OTHER PUBLICATIONS

Written Opinion issued in International Patent Application No. PCT/IB2013/054807 dated Nov. 29, 2013.

\* cited by examiner

FILTRATION ASSEMBLY COMPRISING A FILTER AND A FILTER SUPPORT AND ASSOCIATED METHOD FOR THE COLLECTION AND ANALYSIS OF NANOPARTICLES

TECHNICAL FIELD

The present invention relates to the area of the collection and analysis of the nanoparticles that are likely to be present in suspension in the air.

It relates more particularly to a filtration assembly including a filter having pores that are capable of retaining within them any nanoparticles that are likely to be present in an air flow intended to pass through the filter, and a filter support.

The aim of the invention is to propose maintaining the filter as flat as possible in its support in order to permit the reliable analysis of its surface area, subsequently by X-ray fluorescence, for the analysis of the nanoparticles retained in the filter.

The invention likewise relates to an apparatus and a method for mounting of the filter in its support, thereby making it possible to achieve the aforementioned retention by the filter.

The invention finally relates to an associated method for the collection and the analysis of nanoparticles.

STATE OF THE ART

The rapid expansion of the nanotechnologies makes it essential to undertake further work into the health-related and environmental impacts of these new materials in order to have optimal safety conditions. For some years now nanoparticles, that is to say particles having nanometric dimensions, have been the object of intense research, and their use has begun to spread into various fields such as health, microelectronics, the energy technologies or everyday consumer products such as paints and cosmetics. It is necessary, therefore, to devise methods for the evaluation of the exposure of workers, consumers and the environment to nanoparticles.

The development of reliable methods for the sampling and analysis of aerosols is thus a crucial challenge in terms of public health and the prevention of risks at the work place.

Measurements of the levels of exposure to particles in suspension in the air are usually carried out by weighing the filters before and after the taking of specimens. However, these gravimetric measurements are only reliable for very large quantities of particles (greater than ten, or even a hundred micrograms). Elemental analyses of the ICPMS type are preferred for the determination of smaller quantities. However, this type of analysis calls for the onerous and fastidious preparation of the samples (digestion of the filter, which takes several hours . . . ).

The inventors have also considered utilizing a method of analysis by X-ray fluorescence, in particular with low incidence, which has already been tried and tested, on the one hand by being extremely effective for determining the elemental composition of materials in thin layers and, on the other hand, by making the results of measurement available in a very short space of time, typically in only a few minutes.

The inventors have accordingly arrived at the conclusion that, in order to be able to utilize this technique of analysis by X-ray fluorescence for the analysis of nanoparticles retained by a suitable filter, it was imperative that the latter should be as planar (flat) as possible during the analysis and, incidentally, likewise during the collection, in order to be able to introduce the filter directly after collection into an X-ray fluorescence spectrometer.

To date, however, neither a method nor any commercial device, nor a device that is simply described in the literature, is available which permits filters intended for the collection of particles from the air to be kept flat or, in other words, without folds.

Patent application WO 98/08072 and U.S. Pat. No. 6,779,411 thus describe devices for the collection of particles with filters and filter supports housed in cassettes for sampling the particles. The disadvantages of these devices are numerous. First of all, they do not permit an elemental analysis of the collected particles to be performed without after-treatment. Measurements by gravimetry are performed several times, and analyses by microscopy may likewise be performed after the necessary preparation of a well-located collection zone. In addition, no method or device for the positioning of the filters on their support and in the cassettes is described explicitly in these documents, which leads one to conclude that this positioning is carried out manually. Manual positioning is, in fact, likely to introduce numerous impurities on and around the filter, which are detrimental to a precise and true analysis of the collected particles.

Patent applications FR 2662635 and FR2803238, for their part, describe filters having holes perforated in the thickness of the material, in particular made of a polymer, and the associated methods of their manufacture. No mention is made in these documents of the concrete implementation of these filters in order to achieve the collection per se of the particles. In particular, these patent applications do not describe a filter support, or a means of identification and traceability of the filters once the collection of particles has taken place.

There is a need, therefore, to improve the mounting of filters intended for the collection of nanoparticles on their support, in particular for the purpose of keeping them as flat as possible, and in order to be able to perform the analysis of the collected nanoparticles using an X-ray fluorescence technique.

DISCLOSURE OF THE INVENTION

In order to respond to this need, the invention has as its object a filtration assembly for filtering nanoparticles, including:
  a filter having pores that are capable of retaining within them nanoparticles that are likely to be present in an air flow intended to pass through the filter,
  a filter support including two parts, these being:
    a lower base-forming part including a peripheral bearing surface on which the filter can rest;
    an upper ring-shaped part capable of being mounted around the bearing surface of the base, the mounting of the ring around the bearing surface of the base making it possible to tension the filter in a direction radial to the mounting direction, the mounting clearance between the ring and the bearing surface of the base being dimensioned such as to maintain the filter resting on the bearing surface under mechanical stress by pinching, in a direction radial to the mounting direction.

The expression "peripheral bearing surface" is understood to denote the usual meaning in the mechanical sense, namely a peripheral surface of the base of sufficiently perfect geometry to ensure an integral contact with the filter once mounting has taken place.

The expression "mounting of the ring around the bearing surface" is understood to denote a mechanical mounting of the ring at the external periphery of the bearing surface, the external periphery being configured in order to block the ring mechanically. Advantageously, the ring will become blocked of its own accord by snapping into engagement on the external periphery of the bearing surface.

It goes without saying that, in order to permit pinching of the filter, the diameter of the filter is dimensioned in such a way that it is greater than the sum of the internal diameter of the base and the radial thickness of the bearing surface.

In other words, the invention consists essentially of a solution making it possible both to collect the nanoparticles with the help of a filter having a porosity that has already been put successfully to the test, and to guarantee that the filter will be kept as flat as possible in order to preserve a plane and smooth surface assuring a reliable analysis by X-ray fluorescence, in particular with low incidences.

Once the taking of specimens, in other words the collection of samples or sampling, has been carried out, no manipulation of the filter takes place between collection and analysis, and the filtration assembly may be analyzed by X-ray fluorescence. It may also be stored temporarily inside a box for the purpose of its subsequent analysis. It may finally be destroyed, for example in the case of non-satisfactory collection or in the case of excessively long interim storage.

The ring that has been mounted around the bearing surface of the base of the filter support thus permits it to be tensioned radially, that is to say transversely to the mounting direction, and then to be maintained under tension by pinching without producing folding or creasing of the filter. The tensioned filter is thus maintained in contact against the bearing surface of the base, which delimits the position of the plane of the filter in relation to the support, thereby allowing its subsequent irradiation by X-rays to be performed under a grazing incidence (low incidence, typically lower than 2°) free from any shading effect.

The bearing surface of the base delimits the position of the plane of the filter in relation to the support. In other words, the filter is tensioned and its tensioned surface defines the upper surface of the filtration assembly according to the invention. The filtration assembly may thus be operated with the filter kept flat, for the purpose of its analysis in an X-ray fluorescence apparatus under grazing incidence with a low angle of incidence. In other words, again, the mounting of the filter on the filter support according to the invention permits the filter to be transported and stored without risk to the latter. In particular, the filtration assembly according to the invention may be gripped easily with the aid of pliers on the periphery of the base, and without any risk of contamination of the filter. Furthermore, when the filtration assembly according to the invention is being stored, for example in a box, the filter is not in contact with the bottom of the box because the filter support may advantageously exhibit a certain thickness, typically of a few millimeters, in order to elevate the filter and to avoid any accidental contamination of one of its faces.

Provision may be made advantageously to differentiate the face of the filter intended to collect the nanoparticles from the other opposing face, with the help of a coding system. This coding system may, for example, involve conferring an asymmetrical geometry to the filtration assembly in order to avoid its incorrect positioning in the cassette for taking specimens. A supplementary coding system may likewise be provided at the external periphery of the filtration assembly in order to prevent an operator from turning the filter support and the filter as it is being maintained between the stages of collection of the particles and analysis of the filter by X-ray fluorescence.

According to one advantageous characterizing feature of the invention, the bearing surface of the base and the internal edge of the ring have a radius of curvature of between 0.3 and 0.8 mm. It is stipulated here that the height of the ring is equal to two times the radius of curvature of the internal edge of the latter. Preferably, the radius of curvature of the internal edge of the ring is between 0.3 and 0.6 mm, and that of the bearing surface of the base is between 0.3 and 0.8 mm.

According to another advantageous characterizing feature of the invention, the filter has a thickness of between 10 and 50 μm.

Such radii of curvature permit an effect of pinching sufficient to tension the filter to be obtained in a reliable manner, but without adversely affecting its mechanical and physical properties. Surprisingly, a filter according to the invention, in spite of its very small thickness, does not tear when it is pinched by the ring and does not deform under the stresses imposed by the collection operation per se, provided that it is kept tensioned in the support. The inventors have thus established that the filter remains tensioned without deformation, that is to say is kept as flat as possible, even after several days of collection of nanoparticles at rates of flow in the order of $L \cdot min^{-1}$. This is far from having been obvious, however, having regard, on the one hand, for the very small thickness of the filter as already mentioned above and, on the other hand, for the microporous nature of the filter which gives rise to significant losses of charge in the course of the collection by aspiration of an air flow. A person skilled in the art might have expected the consequence of these significant losses of charge to be a deformation of the filter, or tearing thereof. The inventors have not observed any deformation of the filter in spite of the generated losses of charge of as much as 90 mbar for rates of flow of 1 $L \cdot min^{-1}$.

The mounting of the filter in the support according to the invention is proposed advantageously in order that, once carried out, the two parts of the support are incapable of being disassembled one from the other.

Once assembled and integrated within a cassette for sampling, a filtration assembly according to the invention makes it possible to cause the air flow that it is wished to aspire through the filter to pass through in its entirety. The inventors have not observed any leakage of air around the filtration assembly in a configuration in which it is integrated in a cassette for sampling.

Preferably, the pores of the filter are holes with a calibrated diameter of between 0.05 and 2 μm, and preferably with a density of holes between a number of $10^5$ and $5 \times 10^8$ holes per $cm^2$. The holes may be produced according to various known treatments such as ionic bombardment, treatments with UV, chemical attacks or a combination of these different treatments.

The constituent material of the filter may advantageously be a polymer selected from among the saturated polyesters such as polyethylene terephthalate, polycarbonates, in particular those made from bisphenol A, aromatic polyethers, polysulfones, polyolefins, polyacrylates, polyamides, polyimides, acetates and cellulose nitrates. The filter is preferably made of polycarbonate. Such microporous materials make it possible to achieve retention efficiencies in excess of 99.5% of nanoparticles having a diameter of between 10 and 300 nm, when the latter are in suspension in the air and when the collection rate of flow is between 0.1 and 10 $L \cdot min^{-1}$.

The ring and the base are preferably made from a plastic material selected from among polyethylene terephthalate (PET), polybutylene terephthalate (PBT), polymethyl methacrylate (PMMA), polyamide 6 (PA6), polyamide 66 (PA66), polycarbonate (PC), polypropylene (PP), polyoxymethylene copolymer (POM-C), polyether ether ketone (PEEK). The ring and the base may be produced by injection of a thermoplastic material or by the machining of a block of thermoplastic material.

The one or more plastic material(s) of the ring and of the base may include one or a plurality of additives, in particular additives capable of imparting antistatic properties. The one or more plastic materials may likewise be charged with, for example, glass fibers or carbon fibers.

According to an advantageous characterizing feature, the bearing surface of the base projects for a distance of between 10 and 1500 µm, preferably between 10 and 500 µm, in relation to the ring in the mounted position. The bearing surface of the base preferably projects on its internal periphery.

Advantageously, the base has at the periphery of the bearing surface a plane supporting surface for the ring in the mounted position. This plane supporting surface preferably constitutes the bottom of an accommodating throat for the ring in the base in the mounted position.

According to a preferred variant embodiment, the mounting clearance between the ring and the bearing surface of the base is between 50 and 250 µm. Such a clearance makes it possible to tension a filter easily without the risk of causing it to tear by shearing.

A properly dimensioned radius of curvature around the bearing surface in the bottom of the throat of the base, in particular 0.3 or 0.4 mm, will ensure the effective radial tension of the filter and easy fitting of the ring into the throat of the base.

According to a preferred embodiment, the base has on its periphery an identification area on which an identification label of the filter may be arranged. The identification label is preferably selected from among an alphanumeric code, a bidimensional code, of the data matrix type, an electronic chip such as an RFID tag (English acronym for "Radio Frequency Identification"). The identification label which contains the information relating to the filter and to its support is thus integrated with the filter support. This may be achieved either by a technique known as over injection, or by a pad printing technique, or by gluing, or by an engraving technique.

The expression "over injection" is understood to denote a technique which permits the integration of the label into the base as soon as the latter has been manufactured. The identification label is thus deposited in the interior of a molding tool between the fixed part and the mobile part of the mould. When the mould is closed, the label is applied against the base of the filter support by aspiration, without a gluing or coating medium. In this way, the label perfectly adopts the form of the intended location in the mould and it cannot be torn from the support.

The expression "gluing" is used to denote any method of physical or chemical assembly which makes it possible to assemble two materials by means of a glue or an adhesive.

The expression "pad printing" is used to denote any method of indirect printing which makes it possible to apply the identification label directly onto the base of the support, such as an ink transfer method.

The expression engraving is used to denote any method which makes it possible to hollow out the base of the support, such as a laser marking method, by micro percussion.

The ring may likewise play the role of an antenna for sensing the RFID tag constituted by an electronic circuit distributed on a printed circuit (English acronym PCB for "Printed Circuit Board"), and, in order to do this, may be constituted by a mixture of glass fibers embedded in a resin of the type polyimide, polyester, PVC or Kapton®.

The invention, under another of its aspects, relates to a mounting tool intended for assembling the filtration assembly described above, including:
a platform;
a component forming a clamp, capable of being placed on the platform, for positioning and maintaining the base in position against the platform;
a ring, capable of fitting into the clamp, for guiding and centering the ring around the bearing surface of the base maintained in position against the platform;
a support piece, capable of fitting into the ring, for applying a contact force against the ring guided and centered around the bearing surface.

According to an advantageous embodiment, the mounting tool includes a screw capable of being maintained on the platform in order to be screwed for the purpose of resting against the support piece between a holding position, in which the latter rests against the ring itself in a position in which it is disengaged from the bearing surface of the base, and an extreme mounting position, in which the support piece rests against the ring itself in the mounted position around the bearing surface of the base.

The invention relates, under yet another of its aspects, to a method for mounting the filtration assembly performed by the mounting tool described above, according to which the following stages are carried out:
positioning of the clamp on the platform;
fitting of the base into the clamp;
fitting of the ring into the clamp;
introduction of the filter so that it rests against and is centered against the bearing surface of the base;
fitting the support piece into the ring;
positioning and maintaining the screw on the platform;
screwing the screw so that it rests against the support piece in order to cause the latter to move from its holding position into its extreme mounting position.

The invention relates finally, under a final aspect, to a method for the collection and analysis of nanoparticles, according to which the following stages are carried out:
aspiration of an air flow that is likely to be charged with nanoparticles across the tensioned filter of the filtration assembly as described above;
introduction of the filtration assembly into an X-ray fluorescence spectrometer;
analysis by X-ray fluorescence of the nanoparticles retained by the filter.

Preferably, the rate of aspiration of the air flow through the filter is between 0.1 and 10 $L \cdot min^{-1}$.

DETAILED DESCRIPTION

Other advantages and characterizing features will be appreciated more readily from a perusal of the detailed description, which is provided for illustrative and non-restrictive purposes, with reference to the following figures, in which.

The expressions "lower" and "upper" are to be understood in the sense of the mounting of the filter support from top to bottom and a position of use of the filtration assembly in which the filter is horizontal and the base of the filter support is situated below it.

As illustrated here, a filtration assembly according to the invention, intended for the filtration of nanoparticles, includes a filter support constituted by two components 1, 2, the mutual connection of which permits a filter 3 having pores that are capable of retaining the nanoparticles that are present in an air flow aspirated through the filter to be tensioned and kept flat under mechanical tension.

Although not illustrated here, a filtration assembly according to the invention is intended to be mounted into a cassette for sampling that is adapted to allow the flow of aspirated air to pass through the filter 3 in order to achieve the collection per se of the nanoparticles.

A filter 3 that is used to collect nanoparticles is a microporous membrane, made of polyester, a few tens of microns in thickness and pierced by a multitude of holes with a controlled diameter. By way of example, the holes with a controlled diameter have a diameter of 0.4 μm and exhibit a hole density of $10^5$ perforations per $cm^2$. Such a microporous filter 3 makes it possible to achieve retention efficiencies in excess of 99.5% of the nanoparticles in suspension in the air, having a diameter between 10 and 300 nm, with a collection flow rate of between 0.1 and 10 L·$min^{-1}$.

Figure 1A:
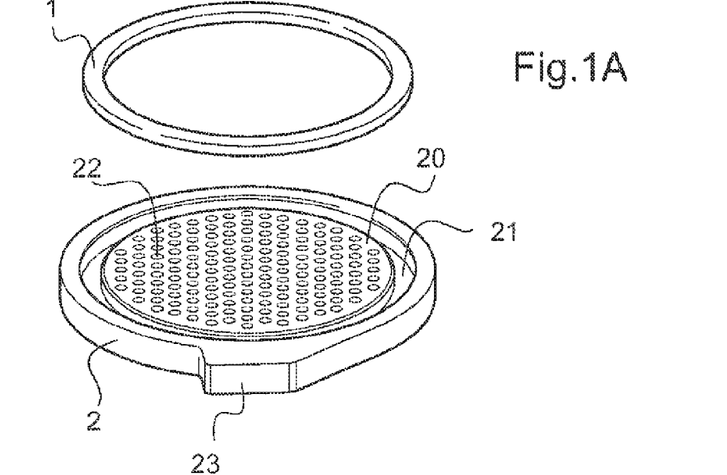
FIG. 1A is an exploded view of the two components constituting a filter support according to a variant embodiment of a filtration assembly according to the invention.
Figures 1B, 1C:
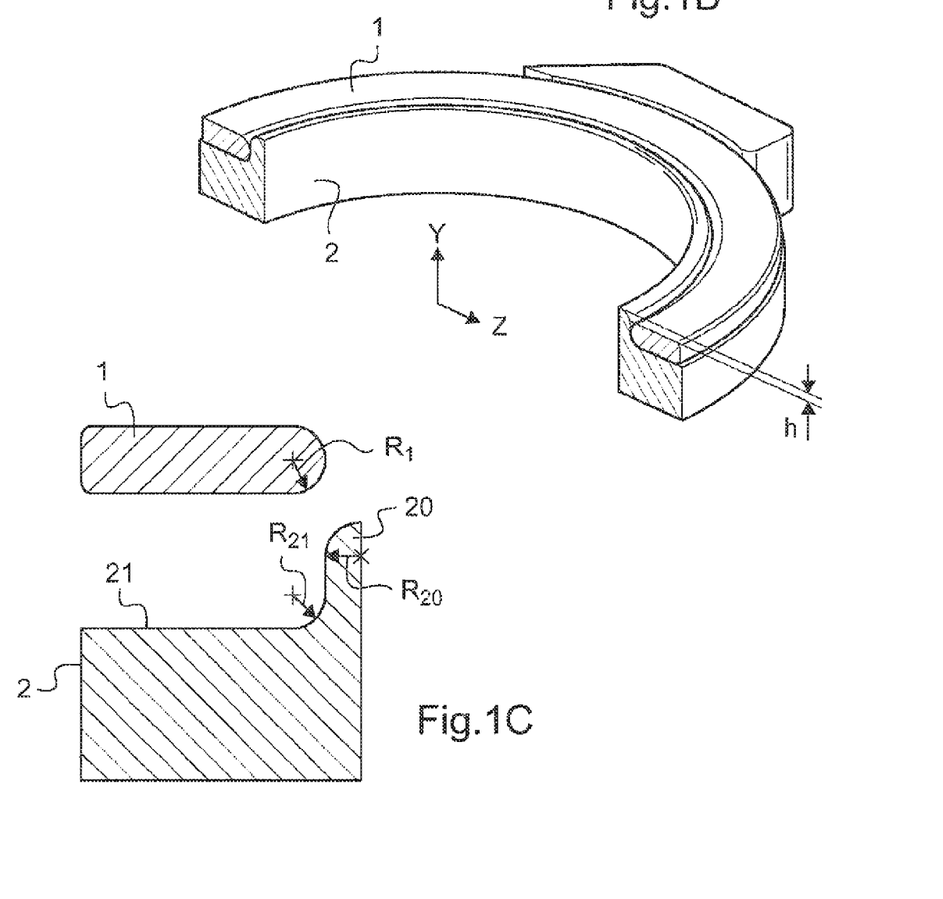
FIG. 1B is a partial view in perspective of an assembled position of the two components constituting a filter support according to a variant embodiment of a filtration assembly according to the invention.
FIG. 1C is a detailed view in cross section of the two components constituting a filter support according to a variant embodiment of a filtration assembly according to the invention.

As illustrated in FIGS. 1A to 1C, the support for the filter according to the invention includes two components 1, 2 that are made from a thermoplastic material.

The upper component is a ring 1 of generally annular shape. The internal edge of the ring 1 exhibits a radius of curvature R1 of 0.5 mm or 0.6 mm.

The lower component forms a base 2 of generally cylindrical shape that is pierced at its center in order to allow the air flow for the aspiration of the nanoparticles to pass. The base 2 exhibits on its internal periphery a cylindrical bearing surface 20 and a face 21 for providing at least one plane support with the ring 1. The base 2 likewise exhibits a radius of curvature of 0.5 mm or 0.6 mm at all angles, such as the radius $R_{20}$ illustrated in FIG. 1C. The radius of curvature $R_{21}$ on the internal surface 21 of the base 2 is 0.3 mm or 0.4 mm so as to tension the filter 3 radially to the mounting direction, as described in detail below, and to permit a good fit.

The base 2 of generally cylindrical shape is asymmetrical and exhibits on its external periphery a protuberance 23 which serves both as a means of coding of the positioning of the assembly according to the invention in a cassette for sampling, and as an identification area on which an identification label of the filter may be arranged. This protuberance 23 may likewise serve advantageously as a means of gripping the filtration assembly for the purpose of its positioning in the subsequent analysis apparatus.

Figure 2A:
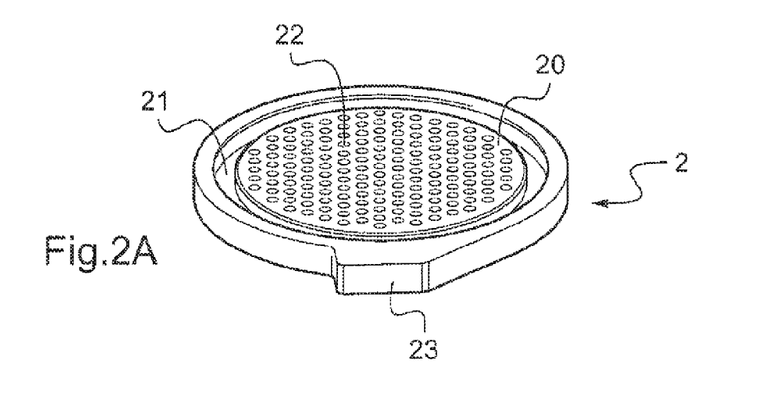
FIGS. 2A to 2C are perspective views according to different variant embodiments of the component forming the base of the filter support according to the invention.

Different variant embodiments of the base 2 may be provided. The base 2 may thus exhibit a central area, in the interior of the peripheral bearing surface 20, in the form of a grille pierced by numerous holes 22 having dimensions in the millimeter range, typically 1 mm in diameter, that are capable of allowing the air flow to pass through the filter 3 (FIG. 2A). The base 2 may exhibit a recessed central area with the plane supporting surface 21 constituting the bottom of an accommodating throat for the ring 1 in the base 2 in the mounted position (FIGS. 2A and 2B), or with the supporting surface 21 being devoid of material around it (FIG. 2C).

According to the invention, the ring 1 is capable of being mounted around the bearing surface 20 of the base 2 in order to permit the filter 3 to be tensioned in a direction Z radial to the mounting direction Y, with a mounting clearance between them dimensioned so as to maintain the filter 3 under mechanical stress by pinching, in contact against the bearing surface 20, in this direction Z radial to the mounting direction Y. The mounting clearance between the ring 1 and the base 2 is preferably equal to five times the thickness of the filter, or 50 to 250 μm depending on the filter being utilized.

The bearing surface 20 of the base 2 thus delimits the position of the plane of the filter 3 in relation to the support. In other words, the filter 3 is tensioned and its tensioned surface defines the upper surface of the filtration assembly according to the invention. The filtration assembly may thus be operated with the filter 3 kept flat, for the purpose of its analysis in an X-ray fluorescence apparatus with grazing incidence with a low angle of incidence.

Figure 2B:
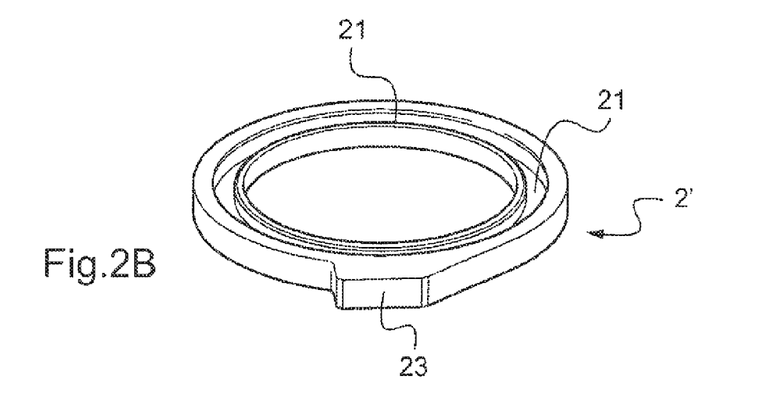
Figure 2C:
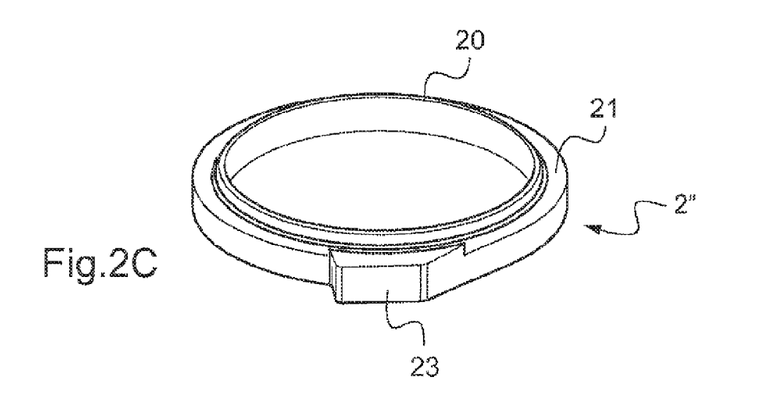

According to the variant embodiment of the base 2, the ring 1 may be inserted completely into the throat of the base (FIGS. 2A and 2B) or may be positioned solely with a plane contact against the supporting surface 21 (FIG. 2C).

The inventors have tested the filtration assembly after assembly. Under experimental conditions with a flow rate of 1 L·$min^{-1}$ and a generated loss of charge in the order of 50 mbar, it has been verified that a filter 3 according to the invention is kept tensioned by the mutual connection between the ring 1 and the base 2. The additional mechanical support that may have been added and is obtained by the grille 22 in FIG. 2A is not necessary. Also, the variant embodiments of FIGS. 2B and 2C are preferred, in order to avoid the potential for disturbances that could interfere with the subsequent analysis of a filter 3 by X-ray fluorescence. On the other hand, the variant embodiment in FIG. 2A may be advantageous in the case of a rate of aspiration of the air flow through the filter or a higher generated loss of charge.

As illustrated in FIG. 1C, the bearing surface 20 of the base 2 is elevated by a height h in the order of 100 μm in relation to the ring 1, once the assembly of the filtration assembly has taken place. This elevation is sufficient to ensure that no other part of the filtration assembly extends above the filter 3, that is to say protrudes in relation to the latter. This makes it possible to have a grazing incidence with a low angle of incidence on the filter 3 during its analysis by the X-ray fluorescence apparatus.

Figure 3:
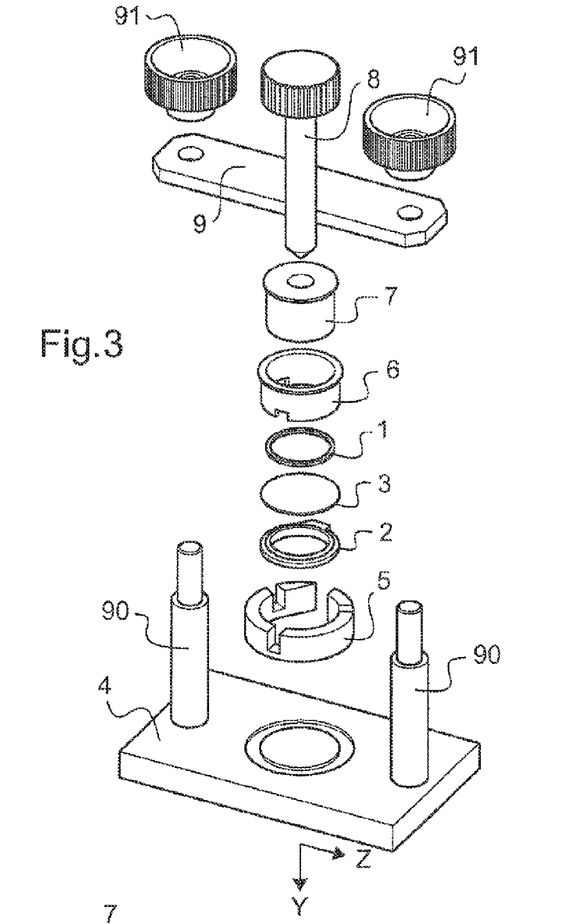
FIG. 3 is an exploded view of the filter and the two components of its support for the filtration assembly according to the invention, and of a mounting tool intended for assembling the said filtration assembly.

In order to be able to perform the assembly of the filtration assembly according to the invention, a mounting tool as illustrated in FIG. 3 has been made available. This mounting tool makes it possible to assemble the ring 1 and the base 2 by tensioning an interposed filter 3 by pinching and by keeping these three components 1, 2, 3 in parallel planes. This makes it possible to avoid the creation of creases and distortions on the filter 3.

The mounting tool thus makes it possible to guarantee the descent of the ring 1 towards the base 2 by tensioning the filter 3, ensuring both the guidance and support and the centering of these components in relation to each other.

The mounting tool depicted here includes, first of all, a platform 4 equipped with vertical arms 90. These arms 90 make it possible to ensure the descent of the cone-point set screw 8 in the direction of assembly Y, that is to say in a direction perpendicular to the platform 4. The role of the screw 8 is described in detail below.

The apparatus likewise includes a component forming a clamp 5 that is capable of being positioned in a throat of the platform 4. This clamp has as its function the positioning of the base 2 of the filter support against the platform 4 and maintaining it in position. The base is thus maintained centered against the contact force exerted by the screw 8 in order to perform the assembly of the components 1, 2, 3 of the assembly as described below.

A ring 6 capable of fitting into the clamp 5 is provided. This ring has as its function the guiding and centering of the ring 1 around the bearing surface 20 of the base 2 that is maintained in position against the platform 4.

The apparatus further includes a support piece 7 capable of fitting into the ring 6. This support piece 7 has as its function the application of a contact force against the ring 1 that is guided and centered around the bearing surface 20 of the base 2.

Finally, in the mounting tool, the assembly of the components 1, 2, 3 of the assembly is assured by the screw 8. This screw 8 is capable of being maintained on the platform 4 by a clamp 9 that is tightened by the two nuts 91. Each of these nuts 91 is capable of being screwed onto one of the vertical arms 90 and of permitting the elements to descend in strictly parallel planes.

Before screwing, stacking is performed by fitting the different components of the apparatus and of the filtration assembly according to the invention, the filter 3 being introduced with care.

Thus, by screwing in the cone-point set screw 8, the latter rests against the support piece 7 between a holding position, in which the latter rests against the ring 1 itself in a position disengaged from the bearing surface 20 of the base 2, and an extreme mounting position, in which the support piece 7 rests against the ring 1 itself in the mounted position around the bearing surface 20 of the base.

Figure 3A:
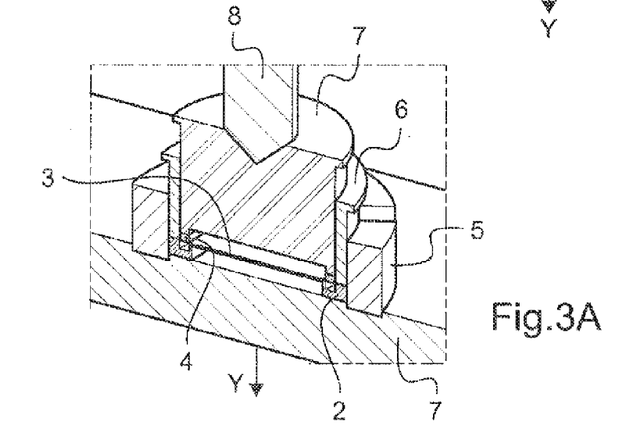
FIG. 3A is a view in cross section depicting in detail a stage in the assembly of the filtration assembly according to the invention by the mounting tool in FIG. 3.

FIG. 3A illustrates an intermediate mounting position, into which the ring 1 begins to be recessed into the throat 21 of the base 2 while tensioning the filter 3 mechanically against the bearing surface 20. It can thus be appreciated in this figure that the support piece 7, which slides into the ring 6 in the course of screwing the screw 8, permits the application of a perfectly controlled force at every point of the ring 1. Each turn of the screw 8 thus causes the parallel planes of each of the components 1, 2, 3 of the filtration assembly according to the invention to move closer together, continuing until the filter 3 is tensioned and maintained between the ring 1 and the base 2.

A number of filters made of different materials in the form of micro porous membranes that are likely to be used as filters 3 of the invention have been tested in order to validate their possible analysis by X-ray fluorescence.

A first test involves charging these different filters with nanoparticles of titanium oxide $TiO_2$ having a density of 14 $\mu g/cm^2$ in atoms of titanium Ti.

Figure 4:
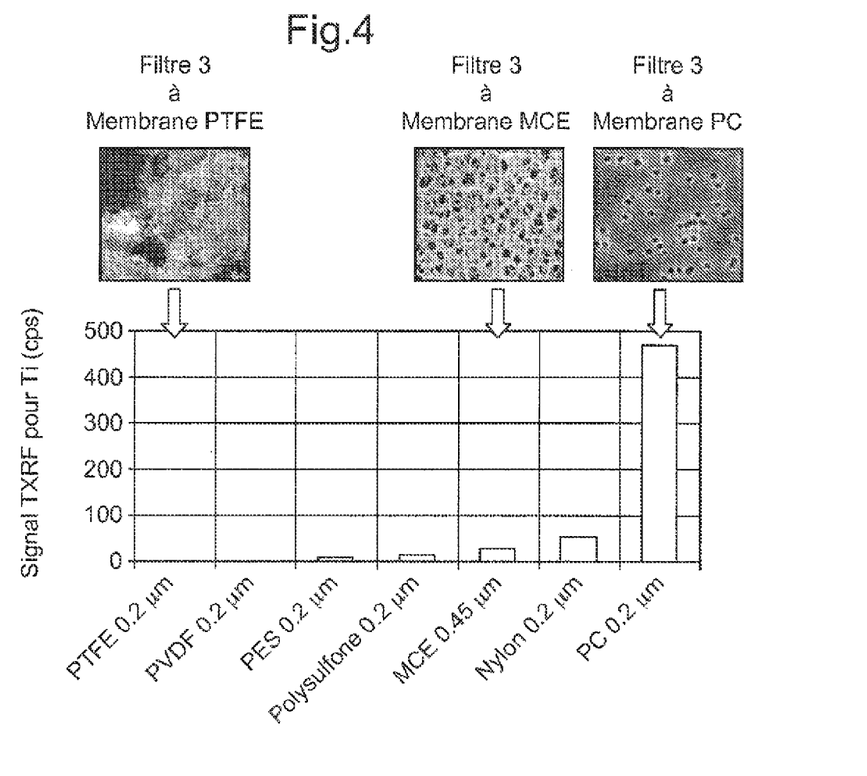
FIG. 4 represents the signal for the measurement by X-ray fluorescence spectrometry of different filters according to the invention.

FIG. 4 illustrates the signal relating to titanium Ti measured by X-ray fluorescence spectrometry for filters made respectively of polytetrafluoroethylene (PTFE), polyvinylidene fluoride (PVDF), polyethersulfone (PES), polysulfone, mixed cellulose esters (MCE), nylon and polycarbonate (PC).

It is clear from a perusal of this FIG. 4 that the most intense signal is obtained for a filter made of polycarbonate (PC). It is also clear that the signal is smaller or zero for filters made of PTFE, PVDF, PBS, polysulfone, MCE and nylon.

A second test involved studying the filtration efficiency depending on the fibrous nature or according to through holes of a membrane constituting a filter. Permeation tests having a plurality of filters made of different materials and having a different nature and a different pore dimension have been performed in this way.

Figure 5:
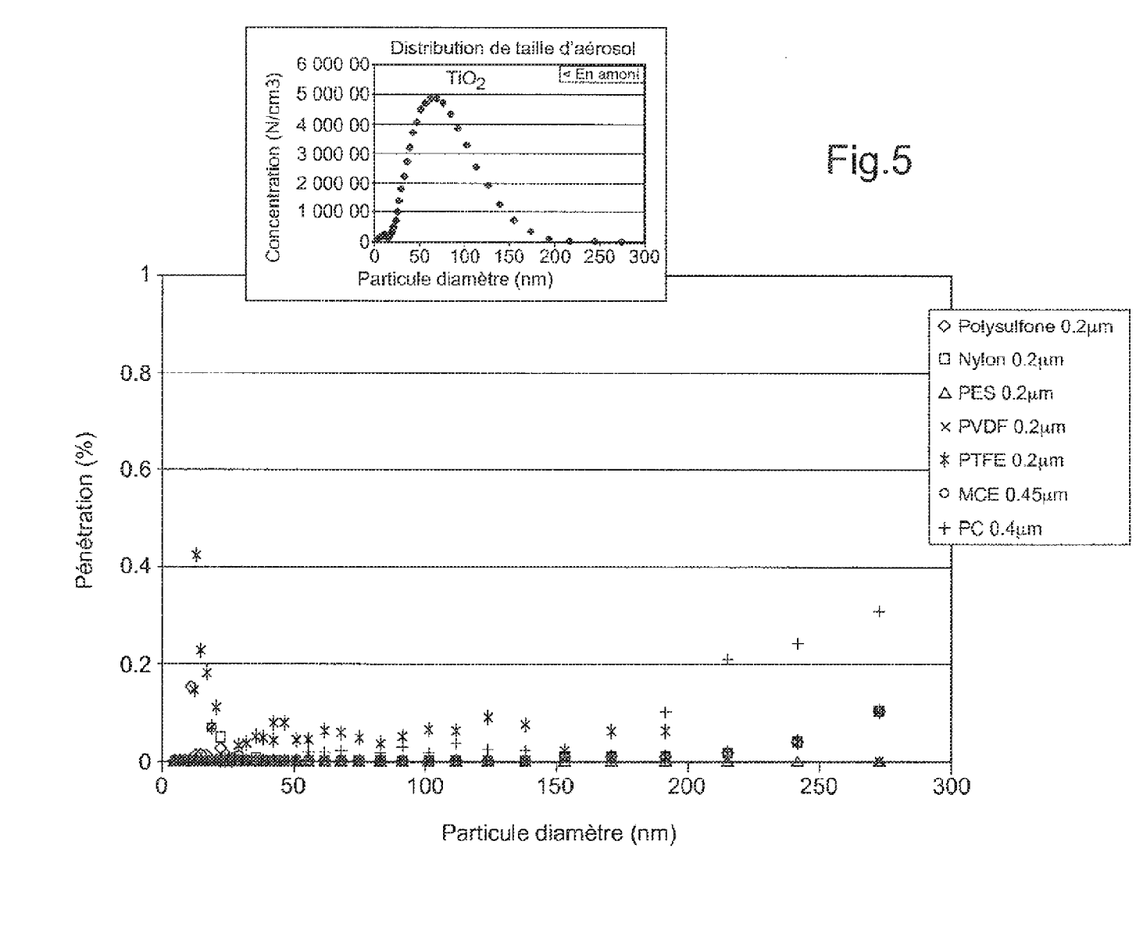
FIG. 5 depicts the retention (rate of penetration) of nanoparticles of titanium oxide $TiO_2$ in a filter according to the invention depending on their diameter.

FIG. 5 thus illustrates the result of these tests: it shows the rate of penetration according to the diameter of the nanoparticles of TiO2 on different filters.

It is clear from a perusal of this FIG. 5 that, for all the tested filters, their retention efficiency is greater than 99.5%, regardless of the diameter of the nanoparticles up to 300 nm.

It is likewise clear that filters made of PC, with holes having a calibrated diameter and a controlled density, have a retention efficiency that is comparable to that of the other tested filters made of a fibrous material.

Figure 6:
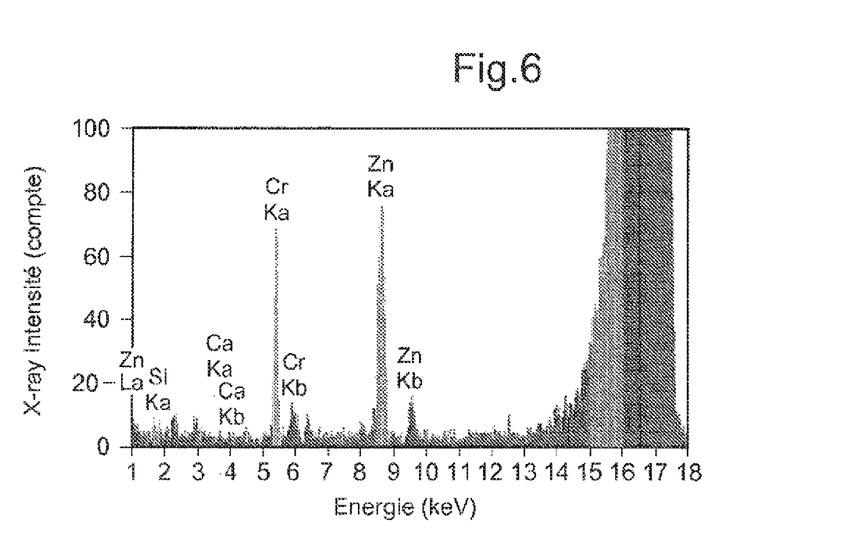
FIG. 6 depicts an X-ray fluorescence spectrum of a filter according to the invention, that has previously been charged with nanoparticles of zinc oxide (ZnO).

Depicted by way of example in FIG. 6 is an X-ray fluorescence spectrum obtained after analysis of a filter made of polycarbonate (PC), charged with nanoparticles of zinc oxide (ZnO), the prior charging density of the filter with nanoparticles being equal to approximately 0.15 $\mu g/cm^2$.

The invention is not limited to the examples described above; it is possible in particular to combine between them characterizing features of the illustrated examples within variants that are not illustrated here.

The invention claimed is:
1. A filtration assembly for filtering nanoparticles, comprising:
   a filter having pores that are configured to retain within them nanoparticles that are likely to be present in an air flow intended to pass through the filter,
   a filter support including two parts, the two parts being:
      a lower cylindrical base including an annular bearing surface at a radially inner periphery of the lower cylindrical base on which the filter can rest, thus delimiting a position of a plane of the filter in relation to the filter support, the lower cylindrical base having a planar support radially outward of the annular bearing surface, the annular bearing surface extending from the planar support in an axial direction of the lower cylindrical base; and an upper ring-shaped part configured to be mounted about an outer periphery of the annular bearing surface of the lower cylindrical base and on the planar support, wherein, in a mounted position of the filter, the upper ring-shaped part is mounted about an outer periphery of the annular bearing surface of the lower cylindrical base and on the planar support, and the annular bearing surface of the lower cylindrical base projects beyond the upper ring-shaped part in the axial direction and is configured (i) to mechanically retain the upper ring-shaped part and (ii) to tension the filter in a direction radial to the mounting direction, a mounting clearance between the upper ring-shaped part and the annular bearing surface of the lower cylindrical base being dimensioned such as to maintain the filter resting on the annular bearing surface under mechanical stress by pinching, in a direction radial to the mounting direction.

2. The filtration assembly as claimed in claim 1, wherein the annular bearing surface of the lower cylindrical base and an internal edge of the upper ring-shaped part have a radius of curvature of between 0.3 and 0.8 mm.

3. The filtration assembly as claimed in claim 1, wherein the filter has a thickness of between 10 and 50 µm.

4. The filtration assembly as claimed in claim 1, wherein the pores of the filter are holes with a calibrated diameter of between 0.05 and 2 µm.

5. The filtration assembly as claimed in claim 4, wherein the density of the holes of the filter is between a number of $10^5$ and $5\times10^8$ holes per $cm^2$.

6. The filtration assembly as claimed in claim 1, wherein the constituent material of the filter is a polymer selected from the group consisting of the saturated polyesters, polycarbonates, aromatic polyethers, polysulfones, polyolefins, polyacrylates, polyamides, polyimides, acetates and cellulose nitrates.

7. The filtration assembly as claimed in claim 6, wherein the filter is made of polycarbonate (PC).

8. The filtration assembly as claimed in claim 1, wherein the upper ring-shaped part and the lower cylindrical base are made from a plastic material selected from the group consisting of polyethylene terephthalate (PET), polybutylene terephthalate (PBT), polymethyl methacrylate (PMMA), polyamide 6 (PA6), polyamide 66 (PA66), polycarbonate (PC), polypropylene (PP), polyoxymethylene copolymer (POM-C), and polyether ether ketone (PEEK).

9. The filtration assembly as claimed in claim 8, wherein the one or more plastic material(s) of the upper ring-shaped part and of the lower cylindrical base include one or a plurality of additives.

10. The filtration assembly as claimed in claim 1, wherein the annular bearing surface of the lower cylindrical base projects for a distance h of between 10 and 1500 µm in relation to the upper ring-shaped part in the mounted position.

11. The filtration assembly as claimed in claim 1, wherein the planar support constitutes the bottom of an accommodating throat for the upper ring-shaped part in the lower cylindrical base in the mounted position.

12. The filtration assembly as claimed in claim 1, wherein the mounting clearance between the upper ring-shaped part and the annular bearing surface of the lower cylindrical base is between 50 and 250 µm.

13. The filtration assembly as claimed in claim 1, wherein the lower cylindrical base has a periphery including an identification area on which an identification label of the filter may be arranged.

14. The filtration assembly as claimed in claim 13, wherein the identification label is selected from the group consisting of an alphanumeric code, a bidimensional code, of the data matrix type and an electronic chip.

15. A method of collection and analysis of nanoparticles according to which the following stages are carried out:
providing the filtration assembly as claimed in claim 1;
aspirating an air flow that is likely to be charged with nanoparticles across the tensioned filter of the filtration assembly;
introducing the filtration assembly into a fluorescence spectrometer X; and
analyzing, by X-ray fluorescence, the nanoparticles retained by the filter.

16. The method of collection and analysis as claimed in claim 15, wherein the rate of aspiration of the air flow through the filter is between 0.1 and 10 $L \cdot min^{-1}$.

* * * * *